(12) United States Patent
Crowley et al.

(10) Patent No.: US 6,394,949 B1
(45) Date of Patent: May 28, 2002

(54) LARGE AREA THERMAL ABLATION

(75) Inventors: Robert J. Crowley, Sudbury; Mark A. Hamm, Lynnfield, both of MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/410,937

(22) Filed: Oct. 5, 1999

Related U.S. Application Data

(60) Provisional application No. 60/103,060, filed on Oct. 5, 1998.

(51) Int. Cl.[7] ............................. A61B 1/00; A61B 18/18
(52) U.S. Cl. ..................... 600/127; 600/104; 600/175; 606/46; 606/48; 606/41
(58) Field of Search ................................. 600/127, 175, 600/104; 606/41, 46, 48–50

(56) References Cited

U.S. PATENT DOCUMENTS

| | | |
|---|---|---|
| 1,963,636 A | 6/1934 | Wappler |
| 2,008,525 A | 7/1935 | Wappler |
| 2,038,393 A | 4/1936 | Wappler |
| 2,090,923 A | 8/1937 | Wappler |
| 2,224,464 A | 12/1940 | Wolf |
| 3,752,159 A | 8/1973 | Wappler |
| 3,835,842 A | 9/1974 | Iglesias |
| 3,850,162 A | 11/1974 | Iglesias |
| 3,901,242 A | 8/1975 | Storz |
| 3,939,839 A | 2/1976 | Curtiss |
| 4,030,502 A | 6/1977 | Iglesias |
| 4,068,667 A | 1/1978 | Iglesias |
| 4,116,198 A | 9/1978 | Roos |
| 4,149,538 A | 4/1979 | Mrava et al. |
| 4,314,559 A | 2/1982 | Allen |
| 4,362,160 A | 12/1982 | Hiltebrandt |
| 4,532,924 A | 8/1985 | Auth et al. |
| 4,538,610 A | 9/1985 | Kubota |

(List continued on next page.)

FOREIGN PATENT DOCUMENTS

| | | |
|---|---|---|
| DE | 24 19 131 | 11/1975 |
| DE | 33 90 567 | 2/1989 |
| DE | 42 42 126 | 7/1994 |
| DE | 196 02 759 | 7/1997 |
| EP | 0 448 857 A1 | 3/1990 |
| EP | 0 481 310 A1 | 10/1990 |
| EP | 0 544 392 A1 | 8/1992 |
| JP | 10328204 | 12/1998 |
| WO | WO 81/03271 | 10/1980 |
| WO | WO 94/05220 | 3/1994 |
| WO | WO 96/23449 | 1/1996 |
| WO | WO 96/26675 | 2/1996 |
| WO | WO 96/30966 | 10/1996 |
| WO | WO 97/15238 | 10/1996 |
| WO | WO 97/17027 | 11/1996 |
| WO | WO 97/17028 | 11/1996 |
| WO | WO 97/23168 | 12/1996 |
| WO | WO 97/24993 | 1/1997 |
| WO | WO 97/16120 | 5/1997 |
| WO | WO 97/49346 | 6/1997 |

OTHER PUBLICATIONS

International Search Report for PCT/US99/23186 dated Feb. 11, 2000.

Primary Examiner—John P. Leubecker
(74) Attorney, Agent, or Firm—Testa, Hurwitz & Thibeault, LLP

(57) ABSTRACT

A large area thermal ablation apparatus for use with an endoscope includes a housing and at least one electrode. The housing is removably attachable to a distal terminating end of the endoscope. The housing includes an outer surface and a cross-sectional area that is at least as large as a cross-sectional area of the distal terminating end of the endoscope. The electrode is supported by the outer surface of the housing. The electrode is capable of delivering energy to a tissue region inside a body to ablate the tissue region.

55 Claims, 4 Drawing Sheets

U.S. PATENT DOCUMENTS

| | | |
|---|---|---|
| 4,565,200 A | 1/1986 | Cosman |
| 4,648,399 A | 3/1987 | Nakada |
| 4,649,917 A | 3/1987 | Karasawa |
| 4,682,596 A | 7/1987 | Bales et al. |
| 4,765,331 A | 8/1988 | Petruzzi et al. |
| 4,823,791 A | 4/1989 | D'Amelio et al. |
| 4,872,458 A | 10/1989 | Kanchira et al. |
| 4,917,082 A | 4/1990 | Grossi et al. |
| 4,936,842 A | 6/1990 | D'Amelio et al. |
| 4,960,106 A * | 10/1990 | Kubokawa et al. ......... 600/127 |
| 4,994,062 A | 2/1991 | Nishigaki et al. |
| 5,007,907 A | 4/1991 | Nishigaki |
| 5,007,908 A | 4/1991 | Rydell |
| 5,045,056 A | 9/1991 | Behl |
| 5,047,027 A | 9/1991 | Rydell |
| 5,057,105 A | 10/1991 | Malone et al. |
| 5,078,717 A | 1/1992 | Parins et al. |
| 5,080,660 A | 1/1992 | Buelna |
| 5,088,998 A | 2/1992 | Sakashita et al. |
| 5,192,280 A | 3/1993 | Parins |
| 5,197,964 A | 3/1993 | Parins |
| 5,277,201 A | 1/1994 | Stern |
| 5,281,218 A | 1/1994 | Imran |
| 5,304,763 A | 4/1994 | Ellman et al. |
| 5,342,357 A | 8/1994 | Nardella |
| 5,354,296 A | 10/1994 | Turkel |
| 5,370,675 A | 12/1994 | Edwards et al. |
| 5,380,320 A | 1/1995 | Morris |
| 5,395,363 A | 3/1995 | Billings et al. |
| 5,403,311 A | 4/1995 | Abele et al. |
| 5,423,812 A | 6/1995 | Ellman et al. |
| 5,423,813 A | 6/1995 | Kaiser et al. |
| 5,435,805 A | 7/1995 | Edwards et al. |
| 5,441,041 A * | 8/1995 | Sauer et al. ................ 600/176 |
| 5,443,470 A | 8/1995 | Stern et al. |
| 5,445,168 A | 8/1995 | Krebs |
| 5,456,689 A | 10/1995 | Kresch et al. |
| 5,458,597 A | 10/1995 | Edwards et al. |
| 5,486,161 A | 1/1996 | Lax et al. |
| 5,486,173 A | 1/1996 | Vancaillie |
| 5,505,730 A | 4/1996 | Edwards |
| 5,508,368 A | 4/1996 | Knapp et al. |
| 5,514,130 A | 5/1996 | Baker |
| 5,527,331 A | 6/1996 | Krescher et al. |
| 5,542,928 A | 8/1996 | Evans et al. |
| 5,549,605 A | 8/1996 | Hahnen |
| 5,549,644 A | 8/1996 | Lundquist et al. |
| 5,556,396 A | 9/1996 | Cohen et al. |
| 5,558,073 A | 9/1996 | Pomeranz et al. |
| 5,558,672 A | 9/1996 | Edwards et al. |
| 5,562,703 A | 10/1996 | Desai |
| 5,562,720 A | 10/1996 | Stern et al. |
| 5,569,241 A | 10/1996 | Edwards |
| 5,575,788 A | 11/1996 | Baker et al. |
| 5,578,007 A | 11/1996 | Imran |
| 5,582,589 A | 12/1996 | Edwards et al. |
| 5,582,610 A | 12/1996 | Grossi et al. |
| 5,599,346 A | 2/1997 | Edwards et al. |
| 5,599,349 A | 2/1997 | D'Amelio |
| 5,630,813 A | 5/1997 | Kieturakis |
| 5,634,924 A | 6/1997 | Turkel et al. |
| 5,653,692 A | 8/1997 | Masterson et al. |
| 5,658,280 A | 8/1997 | Issa |
| 5,667,488 A | 9/1997 | Lundquist et al. |
| 5,669,906 A | 9/1997 | Grossi et al. |
| 5,674,184 A * | 10/1997 | Hassler, Jr. ................. 600/176 |
| 5,683,366 A | 11/1997 | Eggers et al. |
| 5,697,926 A | 12/1997 | Weaver |
| 5,720,719 A | 2/1998 | Edwards et al. |
| 5,746,746 A | 5/1998 | Garito et al. |
| 5,759,183 A | 6/1998 | VanDusseldorp |
| 5,766,168 A | 6/1998 | Mantell |
| 5,766,215 A | 6/1998 | Muri et al. |
| 5,830,146 A | 11/1998 | Skladnev et al. |
| 5,849,011 A | 12/1998 | Jones et al. |
| 5,876,338 A * | 3/1999 | Gilderdale et al. ......... 600/127 |
| 5,925,044 A * | 7/1999 | Hofmann et al. ............. 606/46 |
| 6,004,262 A * | 12/1999 | Putz et al. .................... 606/41 |
| 6,022,313 A * | 2/2000 | Ginn et al. ................. 600/127 |
| 6,059,719 A * | 5/2000 | Yamamoto et al. ......... 600/127 |
| 6,086,583 A * | 7/2000 | Ouchi ........................ 606/41 |

\* cited by examiner

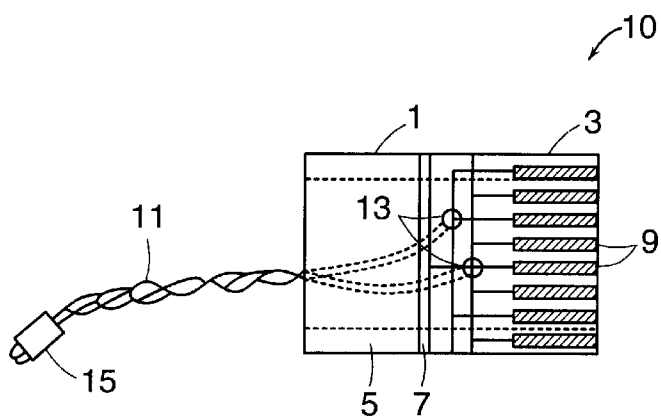
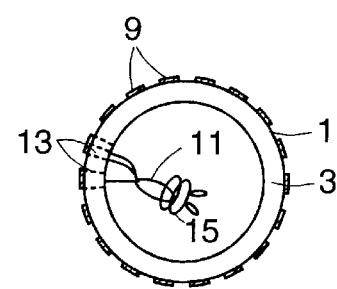
FIG. 1a  FIG. 1b
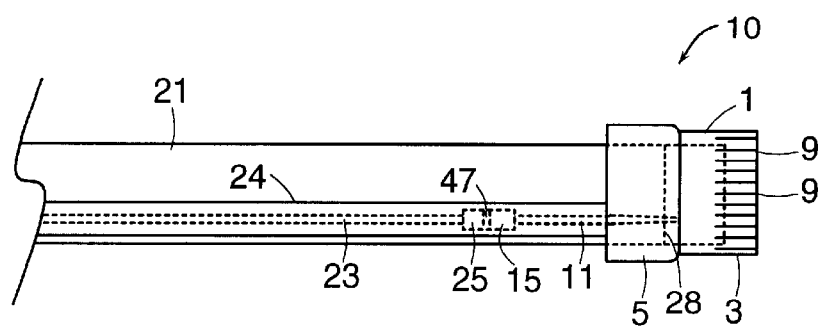
FIG. 2

LARGE AREA THERMAL ABLATION

CROSS-REFERENCE TO RELATED CASE

This application claims priority to and claims the benefit of U.S. provisional patent application Ser. No. 60/103,060 filed Oct. 5, 1998, which provisional application is incorporated herein by reference.

TECHNICAL FIELD

The invention relates to thermal ablation and, more particularly, to a thermal ablation apparatus for use with an endoscope.

BACKGROUND INFORMATION

Thermal ablation of tissue can be performed to remove diseased tissue, such as precancerous or cancerous tissue. For example, thermal ablation has been used in the treatment of Barrett's esophagus, which is a precancerous condition. Thermal ablation can also be performed to remove old tissue and to provide a new surface to support growth of new tissue. Typically, thermal ablation is performed by passing an electrode through a working channel of an endoscope, placing the electrode near the tissue region to be treated and applying radio-frequency (RF) energy to the electrode. An advantage of this technique is that the procedure can be performed under direct visualization. A disadvantage of this technique is that the diameter of the electrode is necessarily limited by the small diameter of the working channel of the endoscope. As a result, the electrode can only treat a small area of the tissue at a time.

In some precancerous conditions that may be treatable via thermal ablation, the area to be treated is relatively large with respect to the electrode, resulting in very long procedure times, irregular or incomplete ablation, and variations in the depth of the ablative effect. The inability to control sufficiently the depth of the ablation procedure can lead to charring or perforation of the tissue or a failure to reduce significantly the number of precancerous cells to a sufficiently low level.

Attempts have been made to provide large electrodes to overcome these limitations. For example, electrodes have been provided on expandable surfaces such as balloons. These apparatuses, however, have been limited to some extent by the diameter of the accessory channel of an endoscope.

SUMMARY OF THE INVENTION

In general, the invention relates to thermal ablation of a large tissue area. Thermal ablation apparatuses, according to the invention, are designed for use with an endoscope.

In one aspect, the invention features an apparatus for use with an endoscope which includes a housing and at least one electrode. The housing is removably attachable to a distal terminating end of the endoscope. The housing includes an outer surface and a cross-sectional area that is at least as large as a cross-sectional area of the distal terminating end of the endoscope. The electrode is supported by at least a portion of the outer surface of the housing. The electrode is capable of delivering energy to a tissue region inside a body to ablate the tissue region.

Embodiments of this aspect of the invention can include the following features.

In one embodiment, the housing comprises an insulator. For example, the housing can comprise a thermal insulator and/or an electrical insulator. At least a portion of the housing can be transparent. Examples of materials suitable for forming the housing include, but are not limited to, a ceramic material, a glass, and a polymeric material. The housing can be substantially ring-shaped. In another embodiment, the housing includes a distal end and a proximal end. The proximal end comprises an elastomeric material and is sized and shaped to slip over the distal terminating end of the endoscope.

In one embodiment, at least one electrode includes a pattern. For example, the pattern can comprise a row of linear elements or a helical pattern. The electrode can be monopolar or bipolar. The housing can include at least one groove and the electrode can be positioned in the groove. The apparatus can further include an electrical conduit in electrical communication with at least one electrode. For example, the electrical conduit can be a wire, a pair of twisted wires, or a coaxial conductor.

In another aspect, the invention features an apparatus for use with an endoscope which includes a sheath, a housing, and at least one electrode. The sheath includes a first channel for receiving the endoscope. The housing is attached to a distal end of the sheath. The housing includes an outer surface and a cross-sectional area at least as large as a cross-sectional area of a distal terminating end of the endoscope. The electrode is supported by at least a portion of the outer surface of the housing. The electrode is capable of delivering energy to a tissue region inside a body to ablate the tissue region.

Embodiments of this aspect of the invention can include the following features.

In one embodiment, the sheath further includes a second channel coextensive with the first channel. An electrical conduit is disposed in the second channel. The electrical conduit is in electrical communication with at least one electrode. In another embodiment, the sheath further includes a second channel coextensive with the first channel for receiving a fluid. The sheath can comprise polyethylene. The sheath can have a thickness in the range from about 0.015 inches to about 0.085 inches.

In another aspect, the invention features a medical apparatus which includes an endoscope, a housing, and at least one electrode. The endoscope terminates at a distal end. The housing is removably attachable to the distal end of the endoscope. The housing includes an outer surface and a cross-sectional area at least as large as a cross-sectional area of the distal end of the endoscope. The electrode is supported by at least a portion of the outer surface of the housing. The housing is capable of delivering energy to a tissue region inside a body to ablate the tissue region.

In another aspect, the invention features a medical apparatus which includes an endoscope, a sheath, and at least one electrode. The endoscope terminates at a distal end. The sheath comprises a channel for receiving the endoscope and a housing attached to a distal end of the sheath. The housing includes an outer surface and a cross-sectional area at least as large as a cross-sectional area of the distal end of the endoscope. The electrode is supported by at least a portion of the outer surface of the housing. The electrode is capable of delivering energy to a tissue region inside a body to ablate the tissue region.

In another aspect, the invention features a method of treating tissue in a body which includes the following steps. A housing is removably attached to a distal terminating end of an endoscope. The housing is removably attachable to the distal terminating end of an endoscope. The housing includes an outer surface supporting at least one electrode on at least a portion of the outer surface and a cross-sectional area at least as large as a cross-sectional area of the distal terminating end of the endoscope. The endoscope and the housing are inserted inside the body near a tissue region to be treated. Energy is applied to at least one electrode to treat the tissue region.

In one embodiment, at least one electrode is connected to a power source through an electrical conduit housed in a channel of the endoscope. In another embodiment, a housing comprising at least one aperture is attached to the distal terminating end of the endoscope and a fluid is provided to the tissue region through the aperture. The fluid can be a cooling fluid, a flushing fluid and/or a conductive fluid. In still another embodiment, the tissue region is illuminated and an optical property of the tissue region is detected.

In another aspect, the invention features a method of treating tissue in a body including the following steps. A sheath comprising a channel for receiving an endoscope and a housing attached to a distal end of the sheath is provided. The housing includes an outer surface supporting at least one electrode on at least a portion of the outer surface and a cross-sectional area at least as large as a cross-sectional area of a distal terminating end of the endoscope. An endoscope is inserted inside the channel of the sheath, such that the housing is positioned near the distal terminating end of the endoscope. The sheath and the endoscope are inserted inside the body near a tissue region to be treated. Energy is applied to at least one electrode to treat the tissue region.

In one embodiment, at least one electrode is connected to a power source through an electrical conduit housed in a second channel of the sheath. In another embodiment, energy is applied to the tissue region to ablate the tissue region.

In another aspect, the invention features a method of manufacturing an ablation apparatus including the following steps. A housing is provided. A slurry comprising a conductive material and a solution is also provided. The slurry is applied to at least a portion of a surface of the housing. The solution is removed from the slurry applied on the surface of the housing to form an electrode comprising the conductive material on the surface of the housing.

In one embodiment, a slurry including a conductive material is printed on the surface of the housing. In another embodiment, the slurry including a conductive material is applied to the housing by spraying, brushing or dipping the housing into the slurry.

In another embodiment, the slurry is heated to remove the solution and to melt or reflow the conductive material.

In yet another embodiment, a housing comprising at least one groove is provided. The solution in the slurry applied to the surface of the housing is removed to form the electrode in the groove of the housing.

The foregoing and other objects, aspects, features, and advantages of the invention will become more apparent from the following description and from the claims.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

FIG. 1a is a side view of a thermal ablation apparatus for use with an endoscope according to one embodiment of the invention.

FIG. 1b is an end view of the thermal ablation apparatus of FIG. 1.

FIG. 2 is a partial cross-sectional view of the thermal ablation apparatus of FIG. 1 mounted at the distal terminating end of an endoscope.

DESCRIPTION

Figure 3:
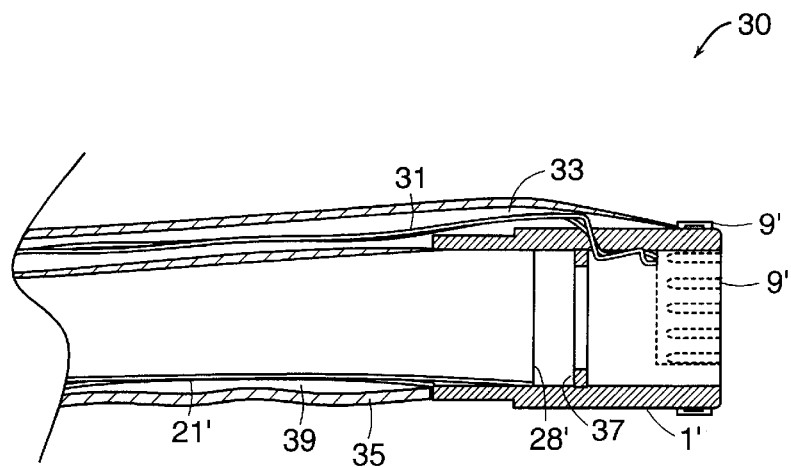
FIG. 3 is a partial cross-sectional view of a thermal ablation apparatus having a coextensive outer sheath arrangement disposed over a typical endoscope, according to one embodiment of the invention.

Referring to FIGS. 1a and 1b, a thermal ablation apparatus 10 includes a housing 1 and multiple electrodes 9 supported by the housing 1. The housing 1 has a distal end 3 and a proximal end 5. The distal end 3 of the housing 1 supports the electrodes 9. The proximal end 5 of the housing 1 is designed to attach removably to a distal terminating end 28 of an endoscope 21, as shown in FIG. 2. The housing 1 is "removably attachable" to the distal terminating end 28 of the endoscope 21 in that the housing 1 can be attached and detached from the distal terminating end 28 of an endoscope 21 any number of times without affecting or changing the functionality of the endoscope 21 itself. The housing 1 is not formed integrally with the distal terminating end 28 of the endoscope 21, but instead is placeable on and removable from the distal terminating end 28 of the endoscope 21 as a separate piece. In one embodiment, the housing 1 has a generally cylindrical shape. In another embodiment, the housing 1 is a cap-like structure.

The distal end 3 of the housing 1 can be constructed of a non-conductive material. A housing 1 made of a non-conductive material provides electrical isolation between multiple electrodes 9 supported by the housing 1. The distal end 3 of the housing 1 can also be constructed of a thermally insulating material. A housing 1 made of a thermally insulating material protects the endoscope 21 from heat generated by the electrodes 9 during an ablation procedure. In some embodiments, the source of the thermal energy can be very close to areas of the endoscope 21 that can be damaged by the thermal energy. Therefore, in these situations, a housing 1 made of thermally insulating material can be essential to ensuring the usefulness of the endoscope 21.

The housing 1 can further be made of an optically transparent material, for example, glass tubing. A housing 1 made of an optically transparent material allows an operator to observe the ablation procedure through spaces between the electrodes 9. Examples of materials suitable for forming the housing 1 include, but are not limited to, ceramic material, glass, and plastic material. In one embodiment, the housing 1 can be made of a ceramic material that can be molded or machined into a suitable shape and subsequently fired to form the housing 1. Advantages of a housing 1 comprising a ceramic material include low heat transfer, low cost and good adhesion properties. In another embodiment, the housing 1 can made of glass that is generally shaped or molded by heat. Advantages of a housing 1 comprising glass is that glass allows an operator the opportunity to observe the ablation procedure. In yet another embodiment, the housing 1 can be made of polymers such as polyimide or polysulfone, or a high temperature epoxy resin such as phenol-formaldehyde resin. The advantage of using these materials is that they can be made to be optically transparent.

The proximal end 5 of the housing 1 can be constructed of an elastomeric material. The elastomeric material can be stretched to slip over the distal terminating end 28 of the endoscope 21 and provide a relatively secure mounting that can still allow flexure between the housing 1 relative to the endoscope 21. Examples of suitable elastomeric materials for constructing the proximal end 5 of the housing 1 include, but are not limited to, silicone and rubber.

An outer diameter of the proximal end 5 can be similar to an outer diameter of the distal end 3 so that the entire housing 1 has a generally uniform diameter. The distal end 3 and the proximal end 5 of the housing 1 can be connected via a lap joint 7. The lap joint 7 provides an overlapping surface for placing an epoxy. The epoxy provides a firm attachment of the proximal end 5 to the distal end 3 of the housing 1. Alternatively, a filament can be tightly tied around the lap joint 7 to provide a firm attachment of the proximal end 5 to the distal end 3 of the housing 1.

Referring to FIG. 2, the distal end 3 of the housing 1 can be relatively short in length to minimize obstruction of the view provided by a typically wide-angle view of the endoscope 21. In one embodiment, the housing 1 does not protrude significantly beyond the distal terminating end 28 of the endoscope 21. The distance between the distal end 3 of the housing 1 and the distal terminating end 28 of the endoscope 21 can be easily adjusted due to a generally cylindrical and coaxial configuration of the housing 1. The housing 1 can be slid into various axial positions along the length of the distal end of the endoscope 21, and further be repositioned as needed. Various types of stops, marks, location dots or the like can be placed along the endoscope 21 or the thermal ablation apparatus 10 to aid alignment of the thermal ablation apparatus 10 and the endoscope 21. Radial positioning of the thermal ablation apparatus 10 relative to the endoscope 21 can also be accomplished by rotating the housing 1 relative to the endoscope 21 with the aid of location marks, stops or other reference points or indicia located on the housing 1 or other portion of the thermal ablation apparatus 10 in such a way as to be easily visible and evident to an operator.

In another embodiment, an articulated housing 1 provides operating flexibility and reduces the need for endoscope 21 manipulation. Articulation of the housing 1 relative to the endoscope 21 can be achieved through the use of a secondary force. Examples of secondary forces include, but are not limited to, water and air pressure. The secondary force can also be a guidewire.

In the embodiment of FIGS. 1a and 1b, an outer surface of the distal end 3 of the housing 1 supports multiple electrodes 9 that are spaced apart and electrically connected to each other. The electrodes 9 are constructed of a conductive material. Examples of suitable conductive materials for forming the electrodes 9 include, but are not limited to, copper foil, gold plating, and sintered or reflown metal and wires. In one embodiment, the electrodes 9 are formed in a pattern for varying the application of energy to a tissue region. For example, the electrodes 9 can form a helical pattern or a dotted, linear pattern. In another embodiment, the patterns comprise a bipolar arrangement of interspersed electrodes. The electrode patterns can be placed around the circumference of the housing 1 or at a distal end 3 of the housing 1. Alternatively, the electrodes 9 can be disposed over a more limited area, angle or position on the housing 1. The shape and thickness of the electrodes 9 can also vary as desired.

The thermal ablation apparatus 10 further includes an electrical conduit 11 connected to the electrodes 9 at a distal end. Referring to FIG. 1b, the electrodes 9 are placed radially from the circumference of the housing 1. The electrodes 9 are connected to the electrical conduit 11 via apertures 13. This arrangement allows all the electrodes 9 to be connected to a power source by an electrical conduit 11 that can be passed through the working channel 24 of an endoscope 21. The electrical conduit 11 has a connector 15 at a proximal end. The electrical conduit 11 can be a pair of wires. The pair of wires can be in the form of a twisted pair such as pigtail wires, as shown in FIG. 1, or a coaxial conductor. Alternatively, the electrical conduit 11 can be a single wire. The wires can be insulated. The connector 15 can be a single pin connector or a multi-pin connector. As shown in FIG. 2, the electrical conduit 11 of the thermal ablation apparatus 10 is A coupled to a second electrical conduit 23 which extends from a power source. The electrical conduit 11 and the second electrical conduit 23 are mated through the connectors 15, 25. The electrical conduits 11, 23 are positioned inside a working channel 24 of the endoscope 21. A fluid sealing ring 47 can be provided at a junction where the two connectors 15 and 25 mate. The fluid sealing ring 47 prevents any fluid from infiltrating the electrical conduits 11, 23 should the working channel 24 accommodate both the electrical conduits 11, 23 and a fluid.

Referring to FIG. 3, a thermal ablation apparatus 30 includes a coextensive sheath 35 having a first channel 39 for receiving an endoscope 21', a housing 1' attached to a distal end of the sheath 35, and multiple electrodes 9' supported by the outer surface of the housing 1'. The endoscope 21' is inserted inside the first channel 39 of the sheath 35, such that the distal terminating end 28' of the endoscope 21' is positioned next to the housing 1'.

In one embodiment, the sheath 35 is long enough to extend along the entire length of the endoscope 21'. Alternatively, the length of the sheath 35 can be shorter than the length of the endoscope 21' such that the proximal end of the endoscope 21' is exposed outside the sheath 35. The sheath 35 can be made of a flexible material that permits some flexure between the sheath 35 and the housing 1', but still maintain a sufficiently fixed relationship between the two. For example, the sheath 35 can be constructed of polyethylene. A sheath 35 made of polyethylene with a wall thickness of about 0.015" to about 0.085" provides reasonable strength and flexibility. In addition, the sheath 35 can be made to conform to the size and shape of the endoscope 21', thus eliminating the need for the housing 1' to have a separate elastomeric proximal end which fits over the distal terminating end 28' of the endoscope 21'. Alternatively, the proximal end of the housing 1' can be designed to fit over the distal terminating end 28' of the endoscope 21'.

In the embodiment of FIG. 3, the sheath 35 has a coextensive second channel 33. The second channel 33 can extend from the distal end of the sheath 35 near the housing 1' through the entire length of the sheath 35 and terminate in a small opening near the proximal end of the sheath 35. The second channel 33 can be used to accommodate an electrical conduit 31 connecting the electrodes 9' to a power source. The second channel 33 can also be used to deliver a fluid to a tissue region or to remove a bodily fluid from a tissue region. Examples of fluids that can be delivered to the tissue include, but are not limited to, cooling, cleaning, flushing, and conducting fluids. The second channel 33 may be formed onto the sheath 35 by coextrusion processes.

The thermal ablation apparatus 30 includes a stop ring 37. The stop ring 37 controls the position of the housing 1' relative to the endoscope 21'. Changing the position of the stop ring 37 relative to the housing 1' changes the position of the housing 1' relative to the distal terminating end 28' of the endoscope 21'. Thus, the further away the stop ring 37 is from the distal end of the housing 1', the further away the distal end of the housing 1' is from the distal terminating end 28' of the endoscope 21'. Therefore, the stop ring 37 can prevent the housing 1' from slipping too far over the distal end of the endoscope 21'. The stop ring 37 can be generally circular in shape. Since the stop ring 37 allows the position of the housing 1' to be altered relative to the distal terminating end 28' of the endoscope 21', the thermal ablation apparatus 30 can be used with a large number of types and various sizes of endoscopes. Different types of endoscopes usable with the thermal ablation apparatus 30 include those used for surgical procedures and for exploratory procedures in areas of the body such as the oral and gastrointestinal tract. The endoscopes can also be flexible or rigid.

Figure 4:
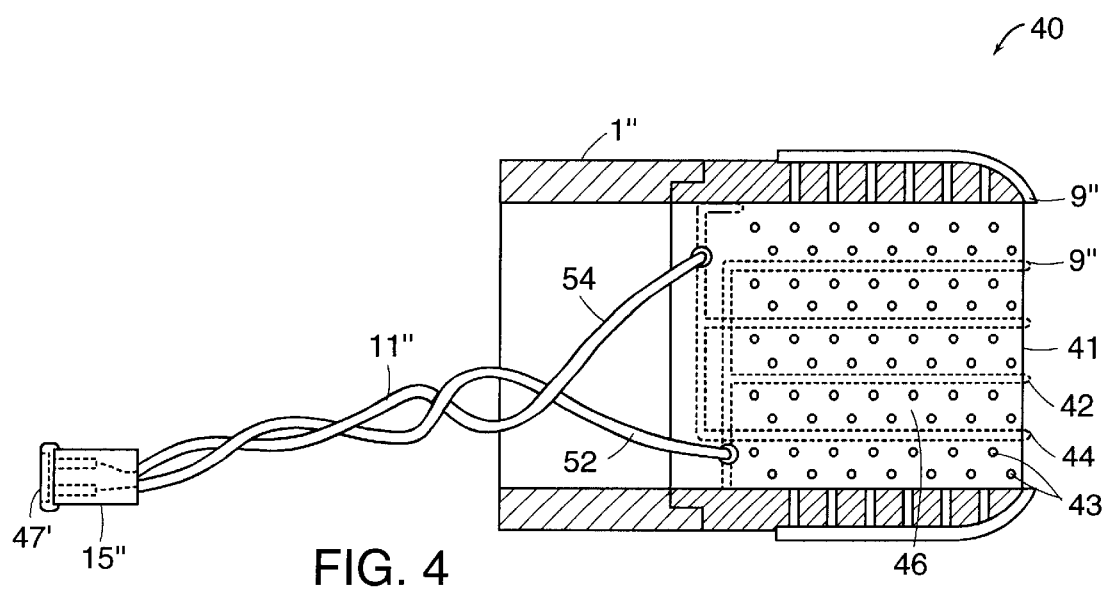
FIG. 4 is a cross-sectional view of a thermal ablation apparatus according to another embodiment of the invention.

FIG. 4 shows another embodiment of a thermal ablation apparatus of the present invention. The thermal ablation apparatus 40 includes a housing 1" having an array of apertures 43 and multiple electrodes 9" provided at the distal end 41 of the housing 1".

This embodiment is useful for thermal ablation procedures performed with a fluid. Examples of fluids used in a thermal ablation procedure include, but are not limited to, cooling, cleaning, flushing and conducting fluids. These fluids can enhance the thermal ablation procedure by cooling and/or cleaning the treatment region by flushing or irrigating with a fluid. Application of a conductive fluid can improve the electrical contact between the electrode 9" and the tissue during the thermal ablation procedure. Saline is an example of a fluid that can be used as a flushing as well as a conducting fluid. The apertures 43 permit the flow of the fluid to the tissue region. The apertures 43 can also permit a bodily fluid to be removed from the tissue region. In one embodiment, the distal end 41 of the housing 1" can be made foraminous by providing pores or apertures 43 to the distal end 41 of the housing 1". For example, a porous ceramic can form the housing 1". Alternatively, plastic or a relatively transparent material such as glass can be made foraminous by drilling microapertures in the material.

The electrodes 9" supported by the outer surface of the housing 1" are interdigitated with alternating electrodes 42, 44. The electrodes 42 are connected to each other and to a wire 52. The electrodes 44 are connected to each other and to a wire 54. The electrodes 42 can be positively charged and the electrodes 44 can be negatively charged. A positively charged electrode 42 is positioned adjacent a negatively charged electrode 44 with an insulator region separating the two electrodes 42, 44. The distance between the electrodes 42, 44 determines the depth of penetration of the ablative energy into a tissue region, since current flows from a negative charged electrode 44 to an adjacent positively charged electrode 42 through a tissue region near the two electrodes 42, 44. The further apart the adjacent electrodes 42, 44 are, the greater the distance the current has to flow through the tissue, thus causing a deeper penetration of the ablative energy into the tissue.

In the embodiment of FIG. 4, the electrodes 42, 44 are placed near the apertures 43, and a conductive fluid can be delivered to a tissue region through the apertures 43. Placing the electrodes 42, 44 near the apertures 43 allows the electrodes 42, 44 to be in close contact with the conducting fluid, permitting an even and controlled application of RF energy to the tissue region. The thermal ablation apparatus 40 includes an electrical conduit 11" connected to electrodes 9" at a distal end. The electrical conduit 11" has an electrical connector 15" at a proximal end. The electrical connector 15" has a sealing ring 47'. The sealing ring 47' prevents fluids such as saline from entering and possibly interfering with the connections between the electrical connector 15" to another electrical connector. The sealing ring 47' can be made of rubber.

Figure 5:
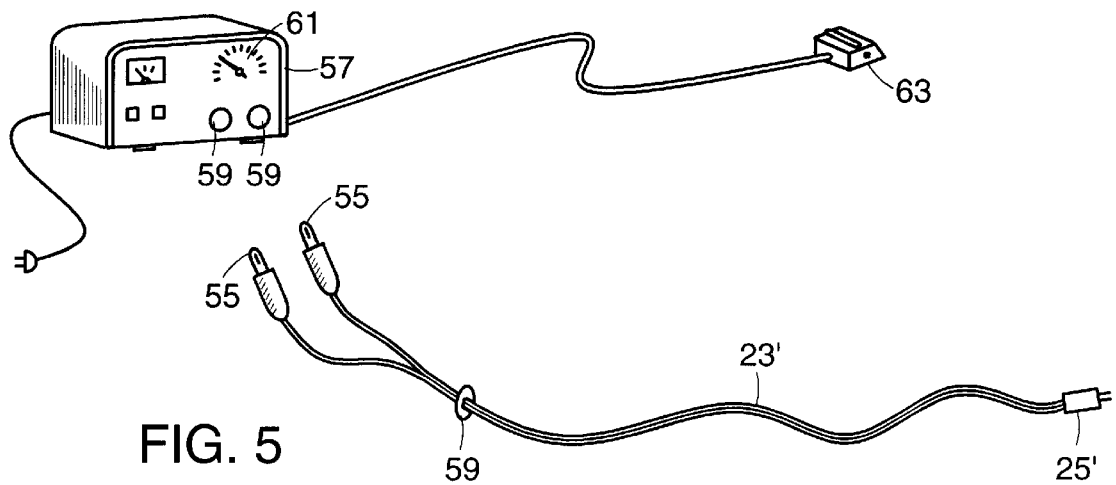
FIG. 5 is a perspective view of a power source and an electrical conduit arrangement for mating with a thermal ablation apparatus according to one embodiment of the invention.

Referring to FIG. 5, an electrical conduit 23' is used for connecting a thermal ablation apparatus (exemplary embodiments of which are shown in FIGS. 1, 3, and 4) to a power source 57. The electrical conduit 23' terminates with a pair of plugs 55 at a proximal end and a connector 25 at a distal end. The plugs 55 can be banana plugs. The electrical conduit 23' also includes a stopper 59 positioned along the electrical conduit 23'. The stopper 59 adjusts the length of electrical conduit 23' placed in the working channel 24 of an endoscope 21, as shown in FIG. 2. The stopper 59 can be made of rubber.

The power source 57 can be a RF energy source. The power source 57 includes jacks 59 to accept the plugs 55, a rheostat 61 to control the duration of the RF energy applied to the thermal ablation apparatus and a floor foot pedal 63 for activating the application of RF energy to the thermal ablation apparatus as desired by the operator.

Prior to performing a thermal ablation procedure, an electrical conduit 23' is passed through the working channel 24 of an endoscope 21, as shown in FIG. 2, so that the distal end of the conduit 23' protrudes from the distal end of the working channel 24 of the endoscope 21. The electrical conduit 23' is allowed to protrude out of the distal terminating end 28 of the endoscope 21 to a length sufficient to allow a person's fingers to mate the connectors 15, 25'. In one embodiment, a stopper 59 provided along the electrical conduit 23' is adjusted prior to passing the electrical conduit 23' through the working channel 24 to control the amount of electrical conduit 23' that is allowed to protrude out the distal end of the endoscope 21. The connectors 15 and 25' are mated, and the electrical conduits 11, 23' are slid back into the working channel 24 of the endoscope 21. The housing 1 is fit over the distal terminating end 28 of the endoscope 21. The plugs 55 at the proximal end of the electrical conduit 23' are plugged into the jacks 59 of the power source 57, if it has not already been done. Under endoscopic guidance, the endoscope 21 and the housing 1 are inserted into a body and positioned near a tissue region to be treated. The thermal ablation apparatus is positioned near the tissue region and RF energy of a selected duration and amplitude is applied to the electrodes 9 to ablate the tissue. In one embodiment, the housing 1 is at least partially transparent and the ablation procedure is monitored through the transparent spaces between the electrodes 9.

Figure 6A:
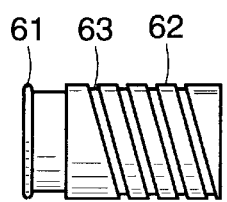
FIG. 6a is a side view of a housing of a thermal ablation apparatus according to one embodiment of the invention.
Figure 6D:
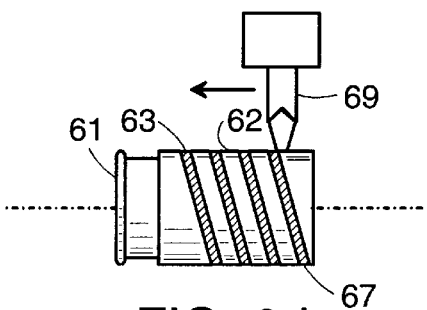
FIG. 6d illustrates another step in a method of manufacturing a thermal ablation apparatus according to one embodiment of the invention.

FIGS. 6a–6d illustrate a method of fabricating an electrode of a thermal ablation apparatus. A housing 61 having grooves 63 is provided as shown in FIG. 6a. The housing 61 can be made of a ceramic, polymeric, or glass material. The grooves 63 can be machined in the housing 61. Alternatively, a base material for the housing 61 can be molded to form the housing 61 with the grooves 63. The grooves 63 define a desired electrode pattern. In the embodiment of FIGS. 6a–6d, the grooves 63 form a helical pattern.

Figure 6B:
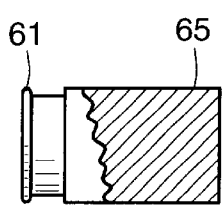
FIG. 6b illustrates a step in a method of manufacturing a thermal ablation apparatus according to one embodiment of the invention.
Figure 6C:
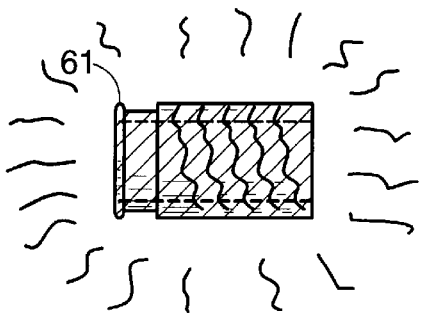
FIG. 6c illustrates another step in a method of manufacturing a thermal ablation apparatus according to one embodiment of the invention.

A slurry 65 comprising a conductive material is applied to the outer surface of the housing 61 as shown in FIG. 6b. The slurry 65 can be applied through any appropriate means such as spraying, dipping, and brushing. The slurry 65 can comprise a water-based weak glue, such as a solution of glycerin and water, mixed with powdered metal. For example, the slurry 65 can include powder made from gold, silver, antimony, or tin. The slurry 65 can also be silver bearing epoxy. In one embodiment, the conductive material included in the slurry 65 has a melting temperature which is lower than a melting temperature of a base material for the housing 61. In another embodiment, the conductive material has low toxicity. The slurry 65 applied to the housing 61 is dried to remove any fluid, gas or other volatile substance contained in the slurry 65. The slurry 65 can be dried at room temperature or at an elevated temperature.

The housing 61 and the dried slurry 65 are heated. Heating burns off any remaining volatile substance in the slurry 65 and melts the conductive material. The molten conductive material flows into the grooves 63 and covers at least a portion of the outer surface of the housing 61. An appropriate duration and temperature of the heating step depends on several factors including the composition of the slurry 65. In one embodiment, heat is applied slowly to reduce the generation of gas bubbles that can cause pinholes or lifting of the conductive material from the housing 61. Subsequent to the heating step, the housing 61 comprising the conductive material is cooled. After cooling, the conductive material is fused to the housing 61. In one embodiment, the housing 61 is cooled slowly or tempered to prevent the conductive material from cracking, peeling, shattering or otherwise breaking away from the housing 61.

Once the housing 61 has cooled, the fused conductive material provided on the protruding surfaces 62 of the housing 61 is removed. The conducting material can be removed by machining. For example, a hardened cutting tool 69 can be moved across the protruding surfaces 62 of the housing 61, as the housing 61 is simultaneously turned to remove the conductive material, as is commonly done in lathe operations. Alternatively, a grinding operation, such as centerless grinding, can be employed to remove the conductive material on the protruding surface 62 of the housing 61.

In other embodiments, the slurry 65 is printed or dispensed over the grooves 63 of the housing 61, eliminating the need for the subsequent machining step. Alternatively, the slurry 65 can be printed or dispensed over a smooth surface of a housing 61, thereby creating conductive regions that are raised above the general surface of the housing 61. An advantage of raising the conductive material above the surface of the housing 61 is improved electrode to tissue contact. A further advantage of using the printing or dispensing method is that it can be a less expensive method of fabrication. For example, the printing of a conductive ink or epoxy, such as silver epoxy, can produce a low cost, albeit somewhat less durable, pattern of conductive material on ceramic, glass, and substrates that cannot withstand the application of very high temperatures such as plastics. In still other embodiments, electroplating conductive materials upon various substrates can be employed in the construction of the thermal ablation apparatus, as long as the electroplated layer is of sufficient conductivity to carry the current and make contact with the subject tissue. The electroplated electrodes on the housing 61 can be further modified by chemical etchings.

The use of electrodes to apply RF energy in ablation procedures is just one useful mode of operation. The housing of the thermal ablation apparatus can also be equipped with spectroscopic, light filtering and light emitting devices for performing tissue spectroscopy.

Figure 7:
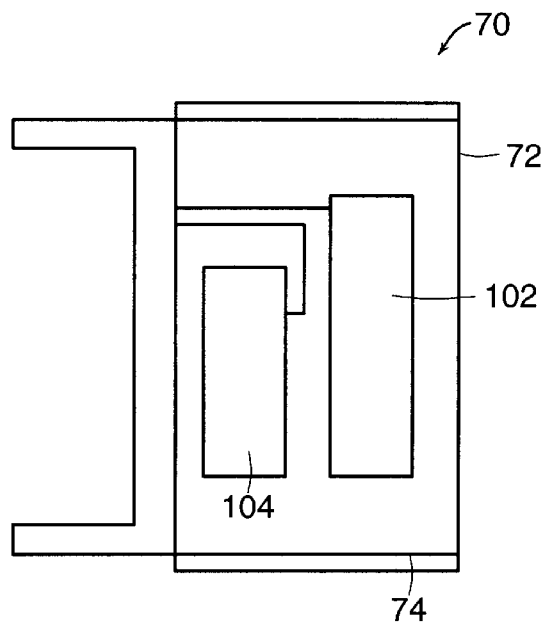
FIG. 7 is a schematic cross-sectional view of a thermal ablation apparatus including a light assembly and a light modulator disposed in a housing according to another embodiment of invention.

Referring to FIG. 7, a thermal ablation apparatus 70 includes a housing 72 which can be removably attached to the distal terminating end of an endoscope. The housing 72 includes a light source 102 and a light modulator 104 disposed in the housing 72, as substantially described in co-pending commonly-owned U.S. patent application Ser. No. 08/939,706 filed on Sep. 9, 1997, the entire contents of which are incorporated herein by reference. The housing 72 further includes at least one electrode 74 supported by the outer surface of the housing 72. The light source 102 illuminates tissue within the body. The light source 102 can include, without limitation, a light emitting diode, a laser, a pulsed light source, a source of ultraviolet energy, or a flashlamp. The light modulator 104 modifies the light emitted by the light source 102. The light modulator 104 can include a filter providing a range of wavelengths to the optical channel of the endoscope. The filter can include, without limitation, an acousto-optic tunable filter, an interference filter, a grating, a prism, a holographic filter, a birefringent filter, or other component that provides a spectral passband. The light modulator 104 can also include a shutter. The shutter, for example, can comprise a liquid crystal device. This embodiment allows the tissue to be characterized by tissue spectroscopy prior to thermal ablation.

Figure 8:
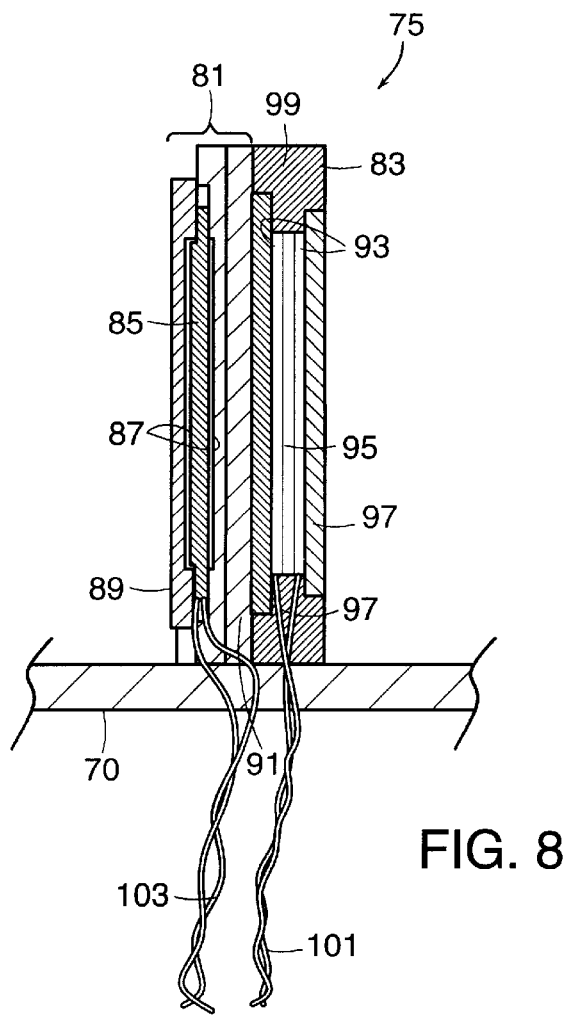
FIG. 8 is a detailed view of the light modulator assembly of the thermal ablation apparatus of FIG. 7.

FIG. 8 shows a detailed light modulator assembly 75 disposed within the housing 72 as shown in FIG. 7. A liquid crystal shutter 81 and an adjacent acousto-optic tunable filter (AOTF) 83 are mounted on a surface of the thermal ablation apparatus 70 with an adhesive. A metal mounting block 99 provides a mounting surface for the individual components of the shutter 81 and the AOTF 83. The AOTF control leads 101 and shutter control leads 103 extend through recess channels (not shown). The liquid crystal shutter 81 includes a liquid crystal 85 located between two electrodes 87. The electrodes 87 can be metalization layers on glass covers 89. When an electric field is applied between the electrodes 87, light passing through the liquid crystal 85 becomes polarized. A polarizing filter 91 is aligned for cross-polarization with the liquid crystal 85 in its active state. Therefore, when an electrical signal is applied to the electrodes 87, optical energy is prevented from passing to the optical channel of the endoscope. An electrical signal can be applied for the duration of the optical pulse from a flashtube in order to momentarily shutter the optical channel.

An electrical signal applied to both sides of the electrodes 93 of the AOTF 83 changes the refractive index of the AOTF crystal 95 and polarizes the transmitted optical energy. Attenuation or selection of specific wavelengths is achieved when the AOTF crystal 95 is used in conjunction with polarizing filters 97. Voltage applied to the electrodes 93 controls the selected wavelength, allowing transmission of specific colors while rejecting other colors.

Thermal ablation apparatuses and procedures of the present invention can be imported to other procedures that can benefit from the application of thermal energy, such as afforded by RF and electrode contact. Procedures such as coagulation and tamponade used to stop bleeding of esophageal varices, ulcerations, and resected margins can also benefit from providing an apparatus which can treat a large tissue region at a time. Other procedures that currently use catheter devices that are small and may not apply enough force over a sufficiently large area can also benefit from the present invention.

The thermal ablation apparatus of the present invention provides several advantages. The proximity of the thermal ablation apparatus to the distal end of the endoscope afforded by the present invention allows for closer and more precise control of the thermal ablative procedure as compared to other procedures performed with conventional methods. The present invention also allows the endoscope to be manipulated by a user to apply firm, even and well controlled pressure, tamponade and directional inputs to the ablation apparatus at the tissue interface. In addition to RF energy, light, heat, and cold (e.g., via cryogenic fluids) can be delivered inside a body by providing appropriate compounds inside a housing which is removably attached to a distal end of an endoscope. A further advantage is that it provides the user the ability to perform procedures quickly, easily and less expensively with a wide variety of endoscopes.

Variations, modifications, and other implementations of what is described herein will occur to those of ordinary skill in the art without departing from the spirit and the scope of the invention as claimed. Accordingly, the invention is to be defined not by the preceding illustrative description but instead by the spirit and scope of the following claims.

What is claimed is:

1. An apparatus for use with an endoscope, comprising:
   a housing removably attachable to a distal terminating end of the endoscope, the housing comprising a distal end, a proximal end, an outer surface and a cross-sectional area at least as large as a cross-sectional area of the distal terminating end of the endoscope, the proximal end of the housing comprising an elastomeric material and being sized and shaped to slip over the distal terminating end of the endoscope; and
   at least one electrode supported by at least a portion of the outer surface of the housing and capable of delivering energy to a tissue region inside a body to ablate the tissue region.

2. The apparatus of claim 1 wherein the housing comprises an insulator.

3. The apparatus of claim 2 wherein the insulator comprises a thermal insulator.

4. The apparatus of claim 2 wherein the insulator comprises an electrical insulator.

5. The apparatus of claim 1 wherein the housing comprises at least one of a ceramic material, a glass, and a polymeric material.

6. The apparatus of claim 1 wherein at least a portion of the housing is transparent.

7. The apparatus of claim 1 wherein the housing comprises at least one groove and the electrode is positioned in the groove.

8. The apparatus of claim 1 wherein the housing is substantially ring-shaped.

9. The apparatus of claim 1 wherein the housing further comprises a stop ring.

10. The apparatus of claim 1 wherein at least one electrode comprises a pattern.

11. The apparatus of claim 10 wherein the pattern comprises a row of linear elements.

12. The apparatus of claim 10 wherein the pattern comprises a helical pattern.

13. The apparatus of claim 1 wherein the housing comprises a plurality of apertures.

14. The apparatus of claim 1 wherein the housing is foraminous.

15. The apparatus of claim 1 further comprising an electrical conduit in electrical communication with at least one electrode.

16. The apparatus of claim 15 wherein the electrical conduit comprises one of wire and coaxial conductor.

17. The apparatus of claim 16 wherein the wire comprises a twisted pair of wires.

18. The apparatus of claim 16 further comprising a connector in electrical communication with a proximal end of the electrical conduit.

19. The apparatus of claim 1 further comprising at least one light source disposed in the housing for emitting light and a light modulator disposed in the housing for modifying light emitted by the light source.

20. The apparatus of claim 1 wherein at least one electrode comprises a monopolar electrode.

21. The apparatus of claim 1 wherein at least one electrode comprises a bipolar electrode.

22. An apparatus for use with an endoscope, comprising:
   a sheath having a thickness in the range from about 0.015 inches to about 0.085 inches and comprising a first channel for receiving the endoscope;
   a housing attached to a distal end of the sheath, the housing comprising an outer surface and a cross-sectional area at least as large as a cross-sectional area of a distal terminating end of the endoscope; and at least one electrode supported by at least a portion of the outer surface of the housing and capable of delivering energy to a tissue region inside a body to ablate the tissue region.

23. The apparatus of claim 22 wherein the sheath further comprises a second channel coextensive with the first channel and an electrical conduit disposed in the second channel, wherein the electrical conduit is in electrical communication with at least one electrode.

24. The apparatus of claim 22 wherein the sheath further comprises a second channel coextensive with the first channel for receiving a fluid.

25. The apparatus of claim 22 wherein the sheath comprises polyethylene.

26. The apparatus of claim 22 further comprising an adjustable stop ring for adjusting a position of the housing relative to the endoscope.

27. The apparatus of claim 22 wherein the housing comprises an insulator.

28. The apparatus of claim 22 wherein at least a portion of the housing is substantially transparent.

29. A medical apparatus, comprising:
an endoscope terminating at a distal end;
a housing removably attachable to the distal terminating end of the endoscope, the housing comprising a distal end, a proximal end, an outer surface and a cross-sectional area at least as large as a cross-sectional area of the distal terminating end of the endoscope, the proximal end of the housing comprising an elastomeric material and being sized and shaped to slip over the distal terminating end of the endoscope; and
at least one electrode supported by at least a portion of the outer surface of the housing and capable of delivering energy to a tissue region inside a body to ablate the tissue region.

30. A medical apparatus, comprising:
an endoscope terminating at a distal end;
a sheath having a thickness in the range from about 0.015 inches to about 0.085 inches and comprising a channel for receiving the endoscope and a housing attached to a distal terminating end of the sheath, the housing comprising an outer surface and a cross-sectional area at least as large as a cross-sectional area of the distal terminating end of the endoscope; and
at least one electrode supported by at least a portion of the outer surface of the housing and capable of delivering energy to a tissue region inside a body to ablate the tissue region.

31. A method of treating tissue in a body, comprising:
a) attaching a housing to a distal terminating end of an endoscope by slipping a proximal end of the housing over the distal terminating end of the endoscope, the housing removably attachable to the distal terminating end of the endoscope, the housing comprising an outer surface supporting at least one electrode on at least a portion of the outer surface and a cross-sectional area at least as large as a cross-sectional area of the distal terminating end of the endoscope, the proximal end of the housing comprising an elastomeric material;
b) inserting the endoscope and the housing inside the body near a tissue region to be treated; and
c) applying energy to at least one electrode to treat the tissue region.

32. The method of claim 31 further comprising connecting at least one electrode to a power source through an electrical conduit housed in a channel of the endoscope.

33. The method of claim 31 wherein step a) comprises attaching a housing comprising at least one aperture and further comprising providing a fluid to the tissue region through the aperture.

34. The method of claim 33 wherein the fluid comprises at least one of a cooling fluid, a flushing fluid and a conductive fluid.

35. The method of claim 31 wherein step a) comprises attaching a housing comprising an insulating material.

36. The method of claim 31 wherein step a) comprises attaching a housing comprising a substantially transparent material.

37. The method of claim 31 wherein step a) comprises attaching a housing supporting a bipolar electrode.

38. The method of claim 31 wherein step a) comprises attaching a housing supporting a monopolar electrode.

39. The method of claim 31 wherein step c) comprises applying RF energy.

40. The method of claim 31 wherein step c) comprises applying energy to ablate the tissue region.

41. The method of claim 31 further comprising illuminating the tissue region and detecting an optical property of the tissue region.

42. A method of treating tissue in a body, comprising:
a) providing a sheath having a thickness in the range from about 0.015 inches to about 0.085 inches and comprising a channel for receiving an endoscope and a housing attached to a distal end of the sheath, the housing comprising an outer surface supporting at least one electrode on at least a portion of the outer surface and a cross-sectional area at least as large as a cross-sectional area of a distal terminating end of the endoscope;
b) inserting an endoscope inside the channel of the sheath such that the housing is positioned near the distal terminating end of the endoscope;
c) inserting the sheath and the endoscope inside the body near a tissue region to be treated; and
d) applying energy to at least one electrode to treat the tissue region.

43. The method of claim 42 further comprising connecting at least one electrode to a power source through an electrical conduit housed in a second channel of the sheath.

44. The method of claim 42 wherein step a) comprises providing a housing comprising at least one aperture and further comprising providing a fluid to the tissue region through the aperture.

45. The method of claim 44 wherein the fluid comprises at least one of a cooling fluid, a flushing fluid and a conductive fluid.

46. The method of claim 42 wherein step a) comprises providing a housing comprising an insulating material.

47. The method of claim 42 wherein step a) comprises providing a housing comprising a substantially transparent material.

48. The method of claim 42 wherein step a) comprises providing a housing supporting a bipolar electrode.

49. The method of claim 42 wherein step a) comprises providing a housing supporting a monopolar electrode.

50. The method of claim 42 wherein step d) comprises applying RF energy.

51. The method of claim 42 wherein step d) comprises applying energy to ablate the tissue region.

52. The method of claim 42 further comprising illuminating the tissue region and detecting an optical property of the tissue region.

53. An apparatus for use with an endoscope, comprising:

a foraminous housing removably attachable to a distal terminating end of the endoscope, the housing comprising an outer surface and a cross-sectional area at least as large as a cross-sectional area of the distal terminating end of the endoscope; and at least one electrode supported by at least a portion of the outer surface of the housing and capable of delivering energy to a tissue region inside a body to ablate the tissue region.

54. A medical apparatus, comprising:

an endoscope terminating at a distal end;

a foraminous housing removably attachable to a distal terminating end of the endoscope, the housing comprising an outer surface and a cross-sectional area at least as large as a cross-sectional area of the distal terminating end of the endoscope; and at least one electrode supported by at least a portion of the outer surface of the housing and capable of delivering energy to a tissue region inside a body to ablate the tissue region.

55. An apparatus for use with an endoscope, comprising:

a housing removably attachable to a distal terminating end of the endoscope, the housing comprising an outer surface, a cross-sectional area at least as large as a cross-sectional area of the distal terminating end of the endoscope;

a light source disposed in the housing for emitting light and a light modulator disposed in the housing for modifying light emitted by the light source, both the light source and the light modulator removable from the endoscope with the housing; and at least one electrode supported by at least a portion of the outer surface of the housing and capable of delivering energy to a tissue region inside a body to ablate the tissue region.

* * * * *

UNITED STATES PATENT AND TRADEMARK OFFICE
CERTIFICATE OF CORRECTION

PATENT NO. : 6,394,949 B1
DATED : May 28, 2002
INVENTOR(S) : Robert J. Crowley and Mark A. Hamm It is certified that error appears in the above-identified patent and that said Letters Patent is hereby corrected as shown below:

<u>Column 12,</u>
Line 50, should read as follows:

-- 18. The apparatus of claim 15 further comprising a connector in electrical communication with a proximal end of the electrical conduit. --

Signed and Sealed this

Tenth Day of September, 2002

*Attest:*

*Attesting Officer*

JAMES E. ROGAN
*Director of the United States Patent and Trademark Office*